United States Patent
Won

Patent Number: 5,503,169
Date of Patent: Apr. 2, 1996

[54] DENTAL FLOSS HOLDER

[76] Inventor: Se K. Won, 6261 Glacier Dr., Westminster, Calif. 92683

[21] Appl. No.: 293,505

[22] Filed: Aug. 22, 1994

[51] Int. Cl.$^6$ ................................ A61C 15/00
[52] U.S. Cl. ................................ 132/325; 132/324
[58] Field of Search ................... 132/323, 324, 132/325, 326, 327, 328

[56] References Cited

U.S. PATENT DOCUMENTS

| | | | |
|---|---|---|---|
| 4,004,599 | 1/1977 | Rosenfeld | 132/325 |
| 4,254,786 | 3/1981 | Won | 132/325 |
| 4,574,823 | 3/1986 | Uriss | 132/325 |
| 4,995,361 | 2/1991 | Lorenzana et al. | 132/324 |
| 5,038,806 | 8/1991 | Ewald | 132/324 |
| 5,199,452 | 4/1993 | Cheng | 132/324 |
| 5,201,330 | 4/1993 | Won | 132/324 |
| 5,253,662 | 10/1993 | Won | 132/324 |

*Primary Examiner*—Cary E. O'Connor
*Attorney, Agent, or Firm*—Robert R. Thornton

[57] ABSTRACT

A dental floss holder is provided with a slot-headed locking axle on which a spool of floss is mounted. A length of floss from the spool disposed within the holder passes through the axle slot and is spanned across two spaced prongs formed on the holder and locked to the axle by being wound on the axle beneath the slotted head after spanning. Tension is selectively manually applied to the spanned floss by the unidirectional rotation of locking cap which is held in position by the slotted head of the locking axle to provide a taut span of floss which can be manipulated between the user's teeth.

4 Claims, 1 Drawing Sheet

U.S. Patent
Apr. 2, 1996
5,503,169
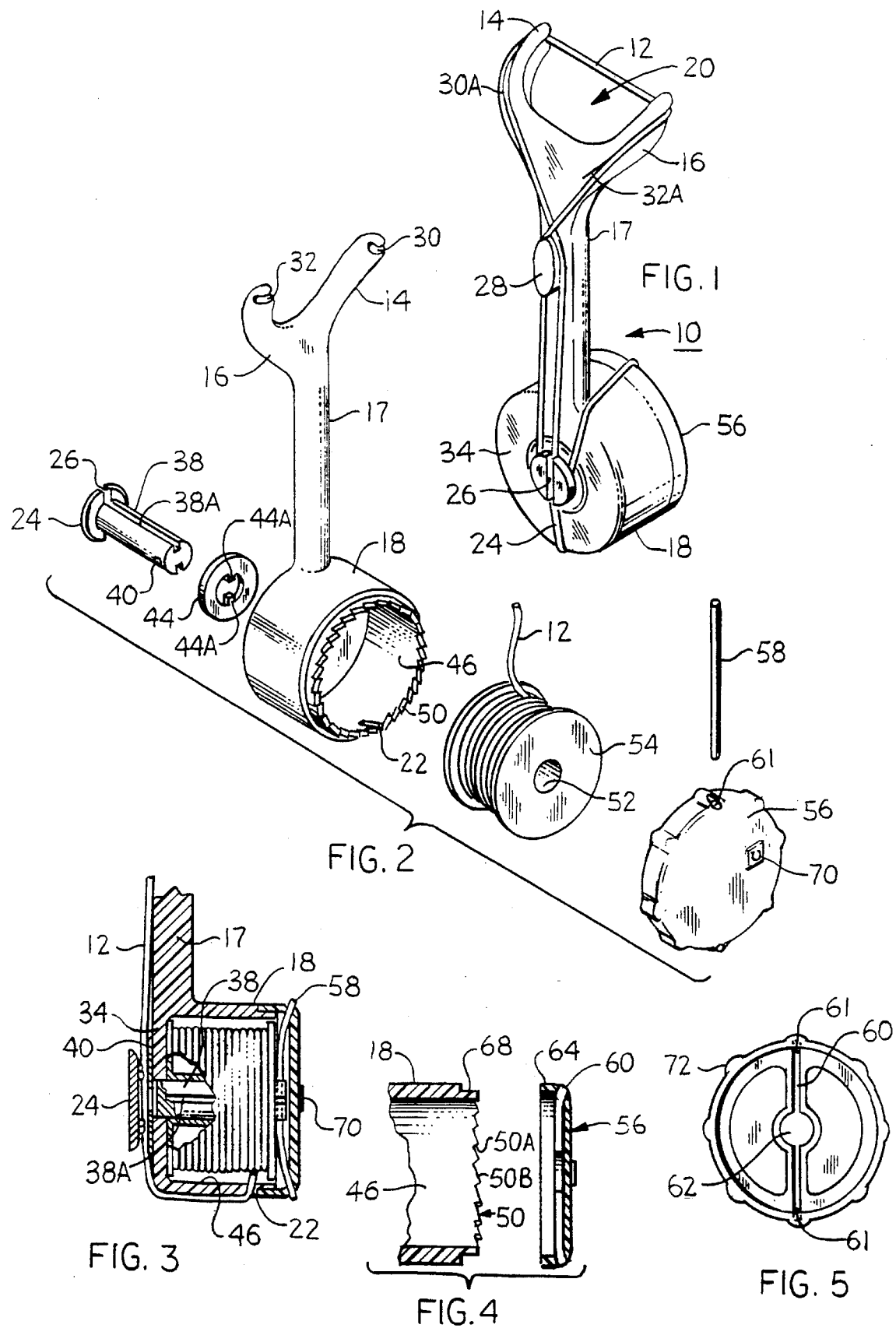

DENTAL FLOSS HOLDER

BRIEF DESCRIPTION OF THE INVENTION

This invention relates to a dental floss holder containing a supply of floss and adapted to provide an exposed section of dental floss maintained under tension for cleaning between the user's teeth and constitutes improvements of such devices as are shown in my prior U.S. Pat. Nos. 4,254,786, issued Mar. 10, 1981; 5,201,330, issued Apr. 13, 1993; and 5,253,662, issued Oct. 19, 1993.

In the holder described in U.S. Pat. No. 4,254,786, a length of floss wound on a spool held within a body member is manually pulled from the spool. When a sufficient length has been unwound, the floss is wound about one side of a slotted head on a locking axle, threaded over two prongs on the holder, and wound about the other side of the slotted head. The locking axle is fixed in position by means of a ratcheting circular spring clip which engages ratcheting recesses formed in the bottom of the body member. Tension is applied to the floss when stretched between the two prongs by rotation of the locking axle. The taut floss can be manipulated between teeth when the holder is held by the user. However, in use, because of the strength of the spring, removal of the spring when it is necessary to replace the spool of floss has been extremely difficult, resulting in user dissatisfaction.

In U.S. Pat. Nos. 5,201,330 and 5,253,662, the ratcheting circular spring clip is replaced by a locking cap formed with a depending lip on the periphery of the cap so as to enclose the body member adjacent the ratcheting recesses. A transverse passageway in the axle contains a pin which extends diametrically across the cap and is fixed thereto. In one embodiment, the pin extends through a pair of diametrically disposed apertures at the depending lip of the cap which are located so as to cause the pin to engage the ratcheting recesses of the body member to permit unidirectional motion of the cap, and so control the tension of the floss. In a second embodiment, to achieve unidirectional rotation of the cap, the cap has a series of complementary ratcheting recesses formed around the inner surface of the depending lip so as to engage the body member ratcheting recesses. In this embodiment, the pin resiliently holds the cap ratcheting recesses against the body member ratcheting recesses, either by being disposed within the cap and extending through a pair of diametrically disposed apertures formed in the depending lip above the ratcheting recesses, or by being disposed in an inwardly curved diametrical groove formed on the exterior surface of the cap so as to extend through an axial aperture formed in the cap and through which the axle extends.

The embodiments of dental floss holders illustrated in the aforesaid patents, while constituting improvements over such devices as were heretofore available in use exhibited certain characteristics which could be further improved. For example, the embodiments which utilized a toothed washer to offset the slotted axle head from the holder body portion were difficult to assemble on the axle. In the embodiment in which the locking pin itself directly engaged the ratcheting recesses, the pin end may occasionally engage the floss slot which was formed radially in the body of the holder, so as to prevent satisfactory operation of the holder. The cap itself may be difficult to turn if wet, due to its smooth peripheral surface. Also, in the embodiment in which the locking pin directly engages the ratcheting recesses, the pin lacked structural support from the cap along its length which would be beneficial in the operation of the holder.

According to the present invention, a dental floss holder has a body member with an axial bore formed therein so as to extend from one side thereof, which is open and on which unidirectional ratcheting teeth are circularly disposed in axial alignment with the bore, to the other body side, which is closed but with a small diameter opening extending therethrough and with a pair of prongs extending outwardly laterally from the body member normal to the bore in a wishbone configuration, each of said prongs having a floss receiving groove formed longitudinally along its outer surface and terminating in a tip across which the groove extends toward the other prong and an axle extending through the body member with a spool holding dental floss mounted on the axle within the body member, and a locking cap of circular cross-sectional configuration complementary to the cross-sectional configuration of the body member, and in which a tangential slot is formed on the body member adjacent the spool so as to extend through the ratcheting recesses for passing the floss from the spool through the body member, and the cap has a hub centrally formed on the interior thereof for receiving a first end of said axle with a transverse channel extending across the interior of the cap so as to be bisected by the hub and a peripheral lip depending from the cap so as to enclose the main body ratcheting recesses when the cap is disposed on the main body member and with a plurality of knobs formed on the external surface of said peripheral lip and with locking cap attaching means connected between said locking cap and said body member for attaching said cap to said axle so as to hold said cap on said main body and including a straight pin extending diametrically across the interior of said locking cap through the transverse channel formed in the interior of said cap and through a transverse passageway formed in said axle and a pair of diametrically oppositely disposed apertures formed in said locking cap and operable to hold opposite end portions of said straight pin extending through said transverse channel against said main body ratcheting recesses and in which the axle has a head at the end thereof opposite said transverse passageway, and including a pair of longitudinal slots formed diametrically opposite one another extending the length of said axle and a washer adapted to be inserted onto said axle and having a pair of teeth extending radially inwardly into the washer opening and adapted to engaged said longitudinal slots of said axle.

BRIEF DESCRIPTION OF THE DRAWING

The invention may be more readily understood by referring to the accompanying drawing, in which:

FIG. 1 is a perspective view of a dental floss holder according to the present invention;

FIG. 2 is an exploded perspective view thereof;

FIG. 3 is a side elevational view, partly in section, thereof;

FIG. 4 is a fragmentary sectional view of a portion of the holder ratcheting mechanism thereof; and FIG. 5 is a bottom plan view of a locking cap for use in the dental floss holder of the present invention.

DETAILED DESCRIPTION OF THE PREFERRED EMBODIMENTS

Referring now to FIG. 1, there is shown a perspective view of a dental floss holder 10 according to the present invention, illustrating the manner in which dental floss 12 is spanned between a first prong 14 and a second prong 16 of the holder. The holder 10 has a body portion 18 which is generally cylindrical and to which the prongs 14 and 16 are connected by a stem 17 so as to be in a "wishbone" disposition and generally normal to the main body 18. A space 20 is formed between the prongs 14, 16 to provide an access way to the spanned floss 12 in order to assist in the flossing operation. A tangential slot 22 (not shown, see FIG. 2) is formed in the body portion 18 opposite the stem 17 to provide a passageway through which the floss 12 emerges from within the body portion 18. As is seen in FIG. 1, the floss 12 passes from the main body portion 18 over a slotted head portion 24 of an axle 38 (see FIG. 2) through a slot 26 formed therein. Then, the floss passes around a floss separator boss 28 formed on the stem 17 and is guided onto the prong 14 and around a prong tip slot 30 (see FIG. 2) by a deep slot 30A. The floss 12 then passes to a similar tip slot 32 formed on the second prong 16. From the tip slot 32, the floss passes through a deep slot 32A formed in the second prong 16 to the floss separator boss 28 on the stem 17 and then to and under the slotted head 24, and around the axle 38, about which the floss 12 is tightly wound, preferably twice, in order to lock the floss between the slotted head 24 and a slotted washer 44 (see FIG. 3) which is held against the main body portion 18 at a generally closed face 34 formed thereon.

Referring now to FIG. 2, the axle 38 which terminates in the slotted head 24 at one end has, at the other end, a transverse passageway 40 formed therein. A slotted washer 44 is mounted on the axle 38 by means of a diametrically opposed pair of slots 38A formed in the axle 38 in which a pair of teeth 44A formed on the inner surface of the washer 44 annulus pass so as to engage the slot 26 so as to prevent axial movement between the washer 44 and the slotted head 24. The floss 12 passes around the axle 38 and is clamped between the slotted head 24 and washer 44. The body portion 18 has a central axial bore 46 formed therein which terminates in a small aperture 48 (see FIG. 3), formed in the generally enclosed face 34 so as to be axially aligned with the central bore 46. At its opposite end, the axial bore 46 opens on to a series of ratcheting recesses 50 formed about the periphery of the body portion 18 opposite the generally closed face 34.

A spool 54 holding the floss 12 is adapted to fit within the axial bore 46. The spool 54 is inserted within the bore 46 so that the axle 38 extends through a central bore 52 in the spool. A locking cap 56 encloses the spool 54 within the bore 46. A locking pin 58 is disposed in a transverse channel 60 formed in the inner face of the locking cap 56 by a pair of apertures 61 so as to extend across a hub 62 formed in the locking cap 56 (see FIG. 5). The axle 38 extends into the hub 62. The pin 58 extends through a pair of diametrically disposed apertures 61 formed in the cap 56 at its ends, and, in its central portion, the pin extends through the aperture 40 in the axle 38. The ends of the pin 58 directionally engage the ratcheting recesses 50 in the body member 18 so as to provide for unidirectional rotation of the cap 56 and so the spool 54 to control the tension on the floss 12, as is described hereinafter.

As is seen in FIG. 4, the ratcheting recesses 50 on the main body portion 18 are unidirectional in nature, that is, each recess 50 has a stop face 50A and a deflection face 50B. The locking cap 56 has a depending lip 64 around the periphery thereof. Immediately within the depending lip 64 are portions of the pin 58 which engage the ratcheting recesses 50 of the main body portion. In other words, when the pin portions engage the ratcheting recesses 50, only unidirectional relative movement between the main body portion 18 and the locking cap 56 is possible. The main body portion 18 has an external shoulder 68 formed adjacent the ratcheting recesses 50 so that the locking cap 56 may be snugly mounted on the main body portion 18 by means of the depending lip 64 enclosing the shoulder 68. The use of the tangential slot 22 avoids the inadvertent locking of the pin in the floss passageway which may occur if a radial slot is used, such as is shown in my prior patents.

Referring back to FIG. 3, the floss holder 10 is shown partially in section, illustrating the means by which the floss 12 is passed from the axial bore 46 around the axle 38 between the slotted head 34 and the washer 44, and from underneath the slotted head 34 to the prongs 14, 16 and back to the slotted head 34, as is shown in FIG. 1. The floss end representing any excess floss after wrapping around the axle 38, is then brought to the face of the locking cap 56 and cut off by means of a cutter blade assembly 70. When it is desired to increase the tension on the floss 12 spanned between the prongs 14 and 16, the locking cap 58 is rotated manually by use of knobs 72 formed on the periphery of the cap 56 so as to increase the tension on the floss 12 in the slot 26.

The dental floss holder 10 of FIGS. 1 through 4 employs a simple locking arrangement to enable the user to readily lock the spanned floss, thereby permitting a tensioned length of floss to be formed quickly and with a minimum of effort for immediate use. In use, the holder 10 is partially inserted into the mouth of the user so that the prongs 14, 16 are disposed, one to the lingual and one to the labial side of the tooth structure to be cleaned. The floss 12 is then worked between adjacent teeth in order to provide the cleaning function. While the teeth are being so cleaned, increased tension may be supplied by rotation of the locking cap as previously described. When the floss has become worn, it is unwound from the slotted head 24 and new floss pulled from the spool 54 and spanned between the prongs 14, 16 and locked by means of the slotted head 24 as previously described. New floss is then available for use in cleaning additional teeth.

The invention claimed is:

1. In a dental floss holder of the type having a body member with an axial bore formed therein so as to extend from one side thereof, which is open and on which unidirectional ratcheting teeth with ratcheting recesses therebetween are circularly disposed in axial alignment with the bore, to the other body side which is closed but with a small diameter opening extending therethrough, a pair of prongs extending outwardly laterally from the body member normal to the bore in a wishbone configuration, each of said prongs having a floss receiving groove formed longitudinally along its outer surface, and each prong terminating in a tip across which the groove extends toward the other prong, an axle extending through the body member, and a spool holding dental floss mounted on the axle within the body member; the combination of a tangential slot formed on the body member and extending through the ratcheting recesses for passing the floss from the spool through the body member;

a locking cap of circular cross-sectional configuration complementary to the cross-sectional configuration of the body member, said cap having a hub centrally formed on the interior of the cap for receiving a first end of said axle, a transverse channel extending across the interior of the cap so as to be bisected by the hub, a peripheral lip depending from the cap so as to enclose the ratcheting recesses when the cap is disposed on the main body member and a plurality of knobs formed on the external surface of said peripheral lip; and locking cap attaching means connected between said locking cap and said body member for attaching said cap to said axle so as to hold said cap in engagement with said main body ratcheting teeth, said locking cap attaching means including a straight pin extending diametrically across the interior of said locking cap through the transverse channel and through a transverse passageway formed in said axle; and a pair of apertures formed in said locking cap so as to be diametrically opposite one another and operable to hold opposite end portions of said straight pin extending through said transverse channel against said main body ratcheting recesses.

2. A dental floss holder according to claim 1, and in which the axle has a head at the end thereof opposite said transverse passageway, and including a pair of longitudinal slots formed diametrically opposite one another extending the length of said axle, and a washer adapted to be inserted onto said axle and having a pair of teeth extending radially inwardly into the washer opening and adapted to engaged said longitudinal slots of said axle.

3. A dental floss holder according to claim 2, and including floss cutting means mounted on said locking cap on the outer side thereof.

4. A dental floss holder according to claim 1, and including floss cutting means mounted on said locking cap on the outer side thereof.

* * * * *